(12) United States Patent　　(10) Patent No.: US 11,593,946 B2
Miyata et al.　　(45) Date of Patent: Feb. 28, 2023

(54) IMAGE-CAPTURING DEVICE AND IMAGE PROCESSING METHOD

(71) Applicant: NICHIA CORPORATION, Anan (JP)

(72) Inventors: Tadaaki Miyata, Yokohama (JP); Hideki Kondo, Yokohama (JP)

(73) Assignee: NICHIA CORPORATION, Anan (JP)

( * ) Notice: Subject to any disclaimer, the term of this patent is extended or adjusted under 35 U.S.C. 154(b) by 302 days.

(21) Appl. No.: 16/902,522

(22) Filed: Jun. 16, 2020

(65) Prior Publication Data

US 2020/0397269 A1　Dec. 24, 2020

(30) Foreign Application Priority Data

Jun. 19, 2019　(JP) ............................. JP2019-113881

(51) Int. Cl.
 *G06T 7/174*　(2017.01)
 *A61B 1/06*　(2006.01)
 (Continued)

(52) U.S. Cl.
 CPC ........ *G06T 7/174* (2017.01); *A61B 1/000094* (2022.02); *A61B 1/05* (2013.01); *A61B 1/0661* (2013.01); *G02B 27/48* (2013.01); *G06T 7/246* (2017.01); *A61B 1/00163* (2013.01); *G06T 2207/30104* (2013.01)

(58) Field of Classification Search
 CPC . A61B 1/000094; A61B 1/00163; A61B 1/05; A61B 1/063; A61B 1/0638; A61B 1/0646; A61B 1/0661; A61B 1/0669; A61B 1/07; G02B 27/48; G02B 5/0263; G02B 5/0278; G06T 2207/10068; G06T 2207/10152; G06T 2207/30104; G06T 7/11; G06T 7/246
 See application file for complete search history.

(56) References Cited

U.S. PATENT DOCUMENTS

2007/0052953 A1* 3/2007 Hill .................... G01N 21/8806
 356/237.2
2007/0100245 A1 5/2007 Kashima
 (Continued)

FOREIGN PATENT DOCUMENTS

JP　2002-165757 A　6/2002
JP　2007-125144 A　5/2007
 (Continued)

*Primary Examiner* — Dakshesh D Parikh
(74) *Attorney, Agent, or Firm* — Foley & Lardner LLP

(57) ABSTRACT

An image-capturing device includes: an illumination light source configured to emit illumination light to illuminate an object; a laser light source configured to emit laser light with a peak wavelength in a range of wavelengths absorbed or reflected by at least one region of the object; an imaging device configured to take an image of the object; a speckle variable device configured to change a speckle pattern in an image acquired by the imaging device over time; and an image processing device configured to process the image acquired by the imaging device, which includes: measuring a change over time in a intensity signal from each pixel constituting the image, and dividing an imaged region of the object into a plurality of portions based on a waveform of the change in the intensity signal over time.

11 Claims, 16 Drawing Sheets

(51) Int. Cl.
*G02B 27/48* (2006.01)
*G06T 7/246* (2017.01)
*A61B 1/05* (2006.01)
*A61B 1/00* (2006.01)

(56) References Cited

U.S. PATENT DOCUMENTS

| | | | |
|---|---|---|---|
| 2011/0317130 A1* | 12/2011 | Gollier | H04N 9/3129 |
| | | | 353/34 |
| 2016/0104292 A1 | 4/2016 | Srinivasan | |
| 2017/0156605 A1* | 6/2017 | Nakao | A61B 5/489 |
| 2019/0045112 A1* | 2/2019 | Ichiki | H04N 5/2258 |
| 2019/0094009 A1 | 3/2019 | Aizawa et al. | |
| 2019/0320127 A1* | 10/2019 | Buckler | H04N 5/378 |
| 2019/0328309 A1* | 10/2019 | Mannoh | A61B 5/0086 |
| 2021/0282655 A1* | 9/2021 | Rege | A61B 5/0261 |
| 2022/0007997 A1* | 1/2022 | Mannoh | G01N 21/6456 |

FOREIGN PATENT DOCUMENTS

| | | | | |
|---|---|---|---|---|
| JP | 2009-136396 A | 6/2009 | | |
| JP | 2014-032371 A | 2/2014 | | |
| JP | 2016-007336 A | 1/2016 | | |
| JP | 2016-221299 A | 12/2016 | | |
| WO | WO-2017/141524 A1 | 8/2017 | | |
| WO | WO-2017141524 A1 * | 8/2017 | | A61B 1/043 |
| WO | WO-2017/175470 A1 | 10/2017 | | |
| WO | WO-2018126114 A2 * | 7/2018 | | A61B 34/20 |

\* cited by examiner

IMAGE-CAPTURING DEVICE AND IMAGE PROCESSING METHOD

CROSS-REFERENCE TO RELATED APPLICATION

This application claims priority to Japanese Patent Application No. 2019-113881, filed on Jun. 19, 2019, the entire contents of which are hereby incorporated by reference.

BACKGROUND

The present disclosure relates to an image-capturing device including a speckle variable device, and an image processing method of sorting regions of an object on the basis of a speckle pattern.

Laser light emitted from laser light sources is coherent and therefore causes strong interference. When laser light is scattered by a scattering medium such as a rough surface, scattered light has a random phase distribution and causes irregular interference. As a result, a fine-scale granular pattern having a high contrast, called a "speckle pattern," is observed.

In the case in which a laser light source is used as a light source for a display device such as a projector or as an illumination light source for a lighting device, speckles are regarded as noise that should be removed or reduced.

Laser speckle contrast imaging (LSCI) has been developed, in which biological tissue having blood cells, which are a scattering medium, is illuminated with laser light, and based on speckles obtained from the biological tissue, the moving speed of blood cells (i.e., blood flow velocity) is measured. In the LSCI technology, speckles are not noise and are used as a "signal" that is needed for the detection of the blood flow velocity.

Japanese Patent Publication No. 2014-32371 discloses a speckle contrast generator that generates speckle noise having a desired speckle contrast when laser light is scattered by a screen.

SUMMARY

There is a need for an image-capturing device and an image processing method to more easily identify regions with different conditions or properties of the surface of an object illuminated with laser light when image information is acquired from the object.

According to one embodiment, an image-capturing device includes: an illumination light source configured to emit illumination light to illuminate an object; a laser light source configured to emit laser light with a peak wavelength in a range of wavelengths absorbed or reflected by at least a region of the object; an imaging device configured to take an image of the object; a speckle variable device configured to change a speckle pattern in an image acquired by the imaging device over time; and an image processing device configured to process the image acquired by the imaging device. The image processing device measures a change over time in an intensity signal from each pixel constituting the image and divides an imaged region of the object into a plurality of portions based on a waveform of the change over time in the intensity signal.

An image processing method in an illustrative embodiment of the present disclosure includes illuminating an object with laser light with a peak wavelength in a range of wavelengths absorbed or reflected by at least a region of the object, taking an image of the object, and dividing an imaged region of the object into a plurality of regions on the basis of a speckle pattern in an image acquired by an imaging device.

In certain embodiment of the present disclosure, an image-capturing device and an image processing method are provided with that an imaged region of an object can be divided into a plurality of portions by changing a speckle pattern over time.

DETAILED DESCRIPTION

Prior to the description of embodiments of the present disclosure, the technical background and the present inventors' findings will be described.

Figure 1:
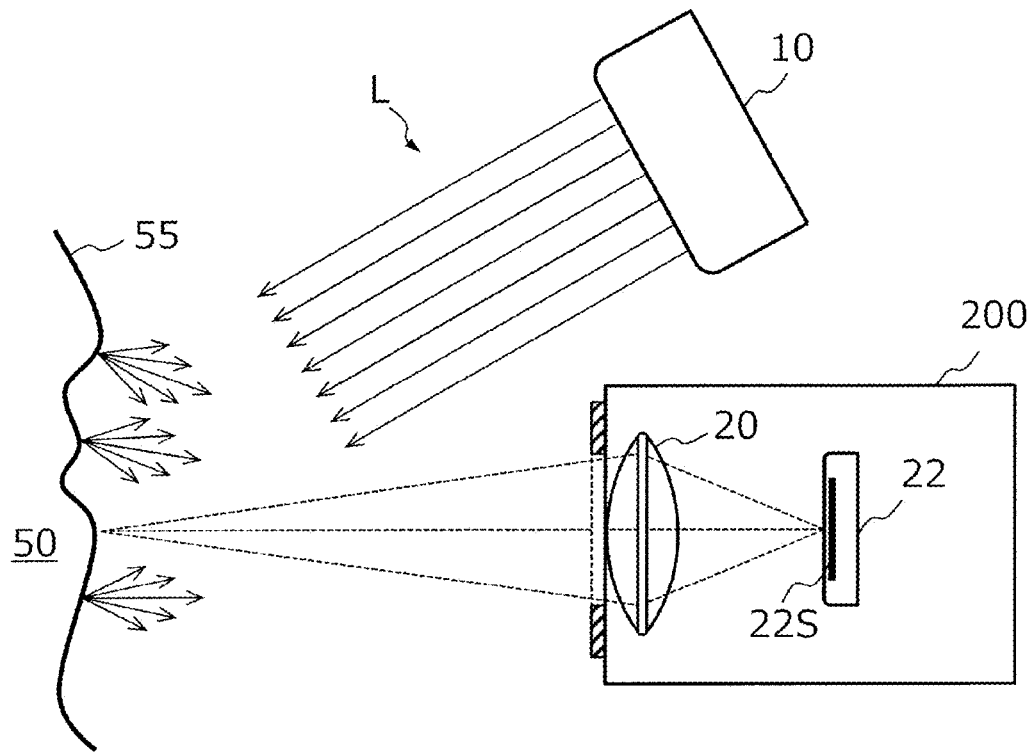
FIG. 1 is a diagram schematically showing a situation in which laser light L emitted from a laser light source 10 is reflected by a surface 55 of an object 50.

Firstly, the formation of speckles by coherent light will be described with reference to FIGS. 1 and 2. FIG. 1 is a diagram schematically showing how laser light L emitted from a laser light source 10 is reflected by a surface 55 of an object 50. The laser light L is highly coherent. The wavelength of the laser light L in the present disclosure is, for example, in the visible light range. The visible light range is, for example, from 380 nm to 750 nm. A typical example of the object 50 is biological tissue. The surface 55 of the object 50 such as biological tissue, and/or a superficial region thereof located on the inside below the surface 55, have irregular microscopic structures as small as about the wavelength of the laser light L. A portion of the laser light L incident on the surface 55 of the object 50 is diffused and reflected by the surface 55. At this time, a portion of the laser light L entering from the surface 55 into the superficial region of the object 50 is absorbed by the superficial region of the object 50, or is returned to the space at the incident side through the surface 55 by multiple scattering. In the case in which the object 50 is biological tissue, even if the surface 55 itself is covered with a smooth mucous membrane, scattering of the laser light L can be caused by cells, intracellular microparticles, etc. The surface 55 and superficial region of the object 50 are also hereinafter collectively referred to as a "scattering portion." The laser light L scattered by the scattering portion and then returned to the incident space is also hereinafter referred to as "scattered light." Spatially random phase is imparted to the scattered light by the fine roughness of the surface 55 and multiple scattering, etc., but the coherence is not lost.

An imaging device 200 includes an imaging optical system 20 including a lens, and an imaging element 22 such as an image sensor. A portion of scattered light generated by the laser light L incident on the surface 55 of the object 50 is collected by the imaging optical system 20 of the imaging device 200 to be converged on an imaging surface (observation plane) 22S of the imaging element 22. An image of the object 50 is formed on the imaging surface 22S by the function of the imaging optical system 20. A bundle of light rays converged at each position on the imaging surface 22S is a superposition of light waves scattered from a corresponding position on the surface 55 and its vicinity. More specifically, when a bundle of light rays from each point on the surface 55 converges on an imaging surface by image formation, the resultant image at each point on the imaging surface has a "point spread distribution" which is determined by a diffraction limit and aberration, etc.

Figure 2:
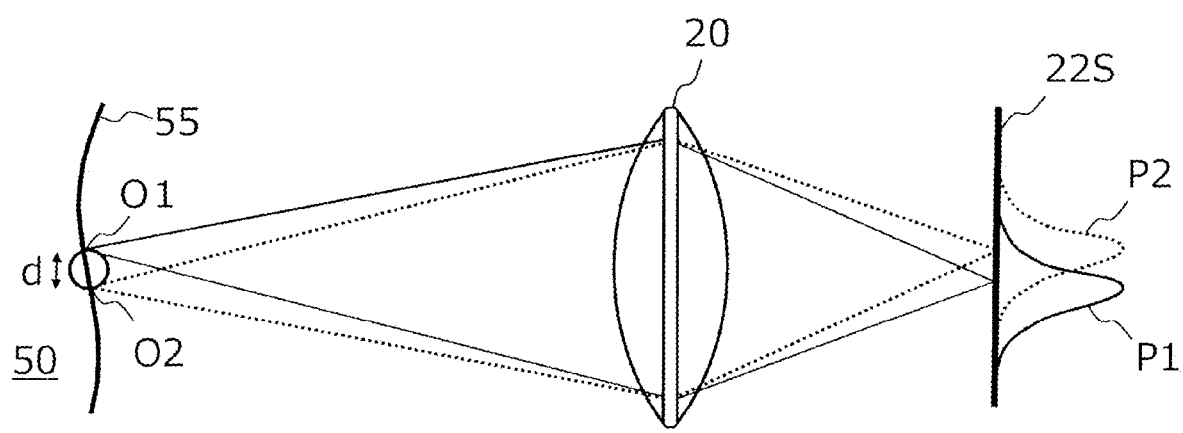
FIG. 2 is a diagram schematically showing a situation in which images of two points O1 and O2 on the surface 55 close to each other are formed on an imaging surface 22S.

FIG. 2 is a diagram schematically showing how images of two adjacent points O1 and O2 on the surface 55 are formed on the imaging surface 22S. The two images of the points O1 and O2 formed on the imaging surface 22S have point spread distributions P1 and P2, respectively, which partially overlap with each other. The size of each point spread distribution P1, P2 is determined by the numerical aperture NA of the imaging optical system 20 and the wavelength $\lambda$ of the laser light L. The "overlap of the two point spread distributions P1 and P2" means that the starting points, i.e., the points O1 and O2, of light rays causing point spreading are located within a distance of not more than the resolution limit of the imaging optical system 20. The length of the resolution limit is indicated by a letter "d". A region whose diameter is the resolution limit d is also referred to as a "resolution region." One resolution region is schematically represented by a circle with a diameter d on the surface 55 of FIG. 2.

In a region where the two point spread distributions P1 and P2 overlap with each other on the imaging surface 22S, rays of scattered light within the resolution region of the object 50 interfere with each other, to thereby form a bright-and-dark pattern depending on phase difference. Such a bright-and-dark pattern depends on the roughness of the surface 55 and the randomness of multiple scattering in a scattering portion of the object 50, and therefore, forms an irregular speckle pattern that can be evaluated using statistics.

Figure 3:
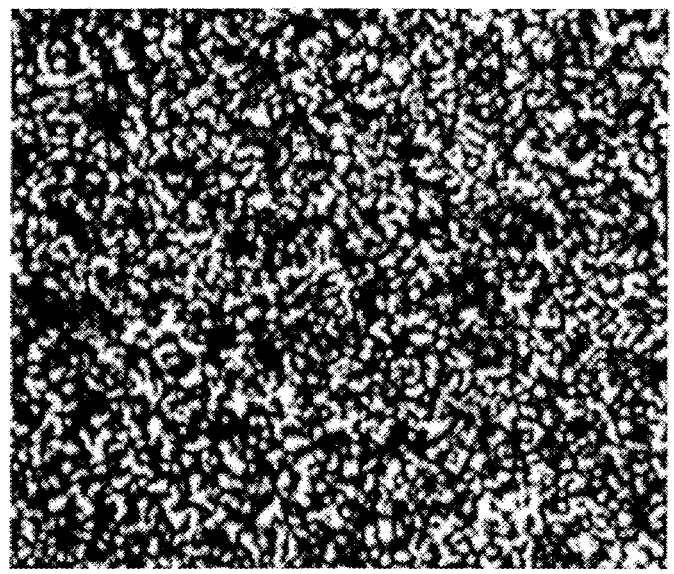
FIG. 3 shows an example of a speckle pattern that may be formed on the imaging surface 22S.

FIG. 3 is a diagram showing an example speckle pattern that may be formed on the imaging surface 22S. In FIG. 3, a fine granular bright-and-dark pattern is observed. Bright portions have a relatively high light intensity, and dark portions have a relatively low light intensity. The minimum size of speckles is substantially equal to the size of a point spread distribution that is determined by the numerical aperture NA of the imaging optical system 20 and the wavelength $\lambda$ of the laser light L.

Interference of scattered light occurs in three-dimensional space. Therefore, the distribution of "electric field amplitudes" defining a speckle pattern inherently depends on three-dimensional position coordinates. Such a speckle pattern that exists objectively in three-dimensional space is called an "objective speckle pattern" or a "non-imaging-system speckle pattern." A speckle pattern observed by the imaging device 200 that depends on the position, orientation, and numerical aperture NA, etc., of the imaging optical system 20, is called a "subjective speckle pattern" or an "imaging-system speckle pattern." Speckles observed by the imaging device 200 are a distribution of the "intensities" of speckles on the imaging surface 22S of the imaging element 22. As used herein, the term "speckle pattern" means a two-dimensional subjective speckle pattern observed by the imaging device 200, unless otherwise specified.

When the object 50, the laser light source 10, and the imaging device 200 of FIG. 1 are at rest, objective speckles and subjective speckles are also at rest. However, when the shape of the surface 55 of the object 50, or cellular tissue in the superficial region of the object 50, is moving, the phase distribution of scattered waves changes with time, and therefore, objective speckles and subjective speckles may also change over time. For example, in the case in which a blood vessel through which red blood cells are flowing exists near the surface of the object 50, the phase distribution of light scattered by the red blood cells changes over time, and the speckle pattern in a region of the imaging surface 22S in which the image of the blood vessel is formed changes over time.

It has been conventionally believed that, for example, in the case in which a laser light source is used as a light source for an endoscope, a speckle pattern is noise in image information and therefore should be removed as much as possible. Therefore, various approaches have been used to reduce the coherence of laser light emitted from a laser light source so that a speckle pattern is not formed.

However, with a light source device according to the present disclosure, a speckle pattern in which the degrees of brightness and darkness vary from region to region of an object under study is intentionally formed, whereby image information that has not conventionally been able to be obtained can be obtained. Specifically, division of an imaged region of the object into a plurality of portions, in other words, segmentation, can be performed on the basis of the speckle pattern that changes over time. Certain embodiments of an image-capturing device of an embodiment of the present disclosure will be described below.

Embodiments

An image-capturing device and an image processing method according to embodiments of the present disclosure will next be described.

Figure 4:
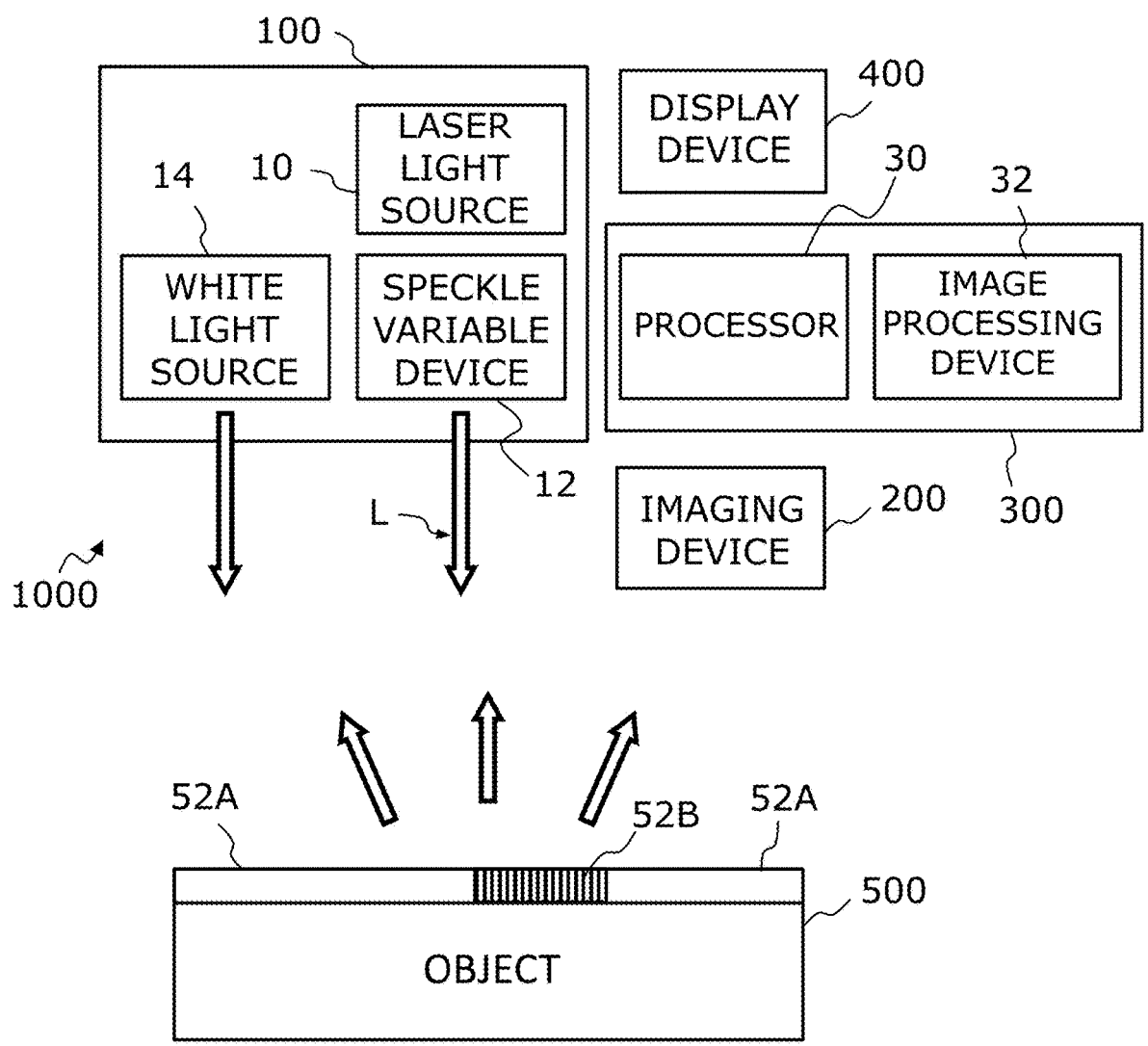
FIG. 4 is a block diagram schematically showing an illustrative constitution of an image-capturing device 1000 including a light source device 100 of an embodiment of the present disclosure.

Firstly, reference is made to FIG. 4. FIG. 4 is a diagram schematically showing an example configuration of an image-capturing device 1000 including a light source device 100 according to this embodiment.

The image-capturing device 1000 of FIG. 4 includes a light source device 100, an imaging device 200, and a controller 300 that is configured to control operations of the light source device 100 and the imaging device 200. The controller 300 is connected to a display device 400. The imaging device 200, the controller 300, and the display device 400 will be described in detail below.

Figure 5:
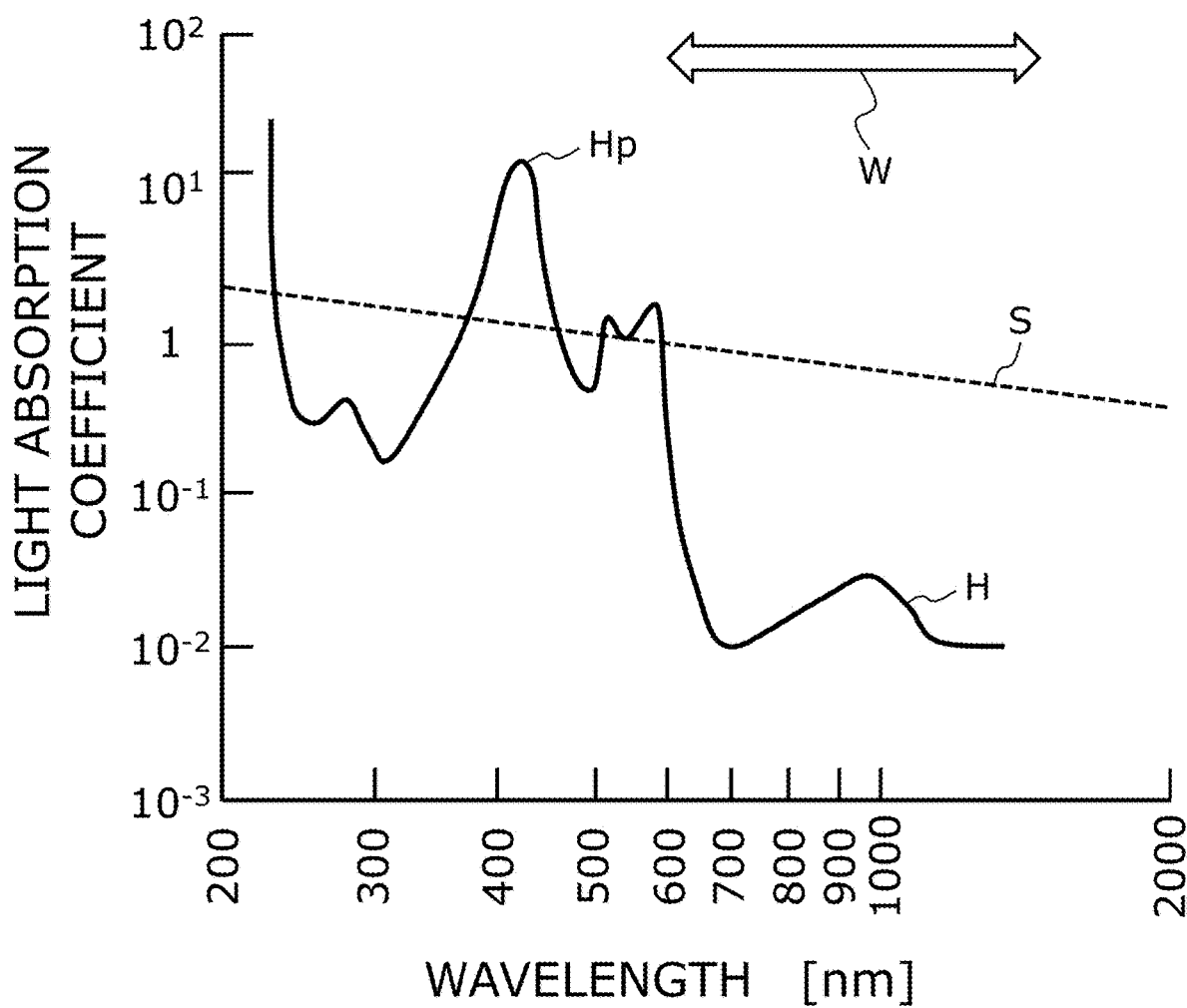
FIG. 5 is a graph showing the wavelength dependence of the absorption coefficient of hemoglobin contained in human blood.

The light source device 100 of this embodiment includes a laser light source 10, and a speckle variable device 12 that is configured to control the coherence of laser light. Examples of the laser light source 10 include a semiconductor laser element (laser diode). The laser light source 10 is configured to emit laser light having a peak wavelength $\lambda$ within a wavelength range of light which is relatively strongly absorbed or relatively strongly reflected by a region 52B of an object 500 under study, compared to the other region 52A. The laser light source 10 emits coherent laser light, and therefore can form speckle patterns having different speckle contrasts in the regions 52A and 52B of the object 500. The regions of the object 500 can also be referred to as a first region and a second region. As used herein, for example, the term "forming a speckle pattern in the region 52A" means "a speckle pattern is formed in the image of the region 52A in the image acquired by the imaging device 200." The speckle pattern formed in the image of the region 52A is based on interference of scattered light occurring in the region 52A. Hence, in the case in which the region 52A and the region 52B of the object 500 are different in absorption and reflection characteristics and scattering characteristics of laser light relative to the peak wavelength $\lambda$, the distinguish or recognition of the region 52A and the region 52B can be achieved on the basis of features extracted from the speckle pattern over time FIG. 5 is a graph showing the wavelength dependence of the light absorption coefficient of hemoglobin. Hemoglobin is a protein in red blood cells that is found in the blood of all vertebrates, including humans. In FIG. 5, the light absorption coefficient of hemoglobin is indicated by a solid line H. In FIG. 5, for reference, the scattering coefficient of human body tissue is indicated by a dashed line S. As shown in FIG. 5, hemoglobin relatively strongly absorbs light having a wavelength in the region of about 400 nm to about 600 nm, compared to the infrared region. In particular, hemoglobin has a distinctively high light absorption coefficient at a wavelength of about 415 nm, which indicates a light absorption peak Hp. In the region where the wavelength exceeds 1000 nm, the light absorption coefficient of water (not shown) sharply increases. In the wavelength range of about 650 nm or more and about 1350 nm or less indicated by an open arrow indicated by a reference character W, the light absorption of hemoglobin or water is relatively low, and therefore, scattering is more likely to occur. Therefore, light in the wavelength range W indicated by the open arrow of FIG. 5 penetrates deep into a living body compared to light with the other wavelength ranges. The wavelength range W is called a "biological window." To obtain information from the inside of human biological tissue, the biological tissue is illuminated by light having a wavelength in the wavelength range W. For such purposes, incoherent light, which is less likely to cause speckle noise, has been conventionally used.

FIG. 5 is a graph showing the wavelength dependence of the light absorption coefficient of hemoglobin. Hemoglobin is a protein in red blood cells that is found in the blood of all vertebrates, including humans. In FIG. 5, the light absorption coefficient of hemoglobin is indicated by a solid line H. In FIG. 5, for reference, the scattering coefficient of human body tissue is indicated by a dashed line S. As shown in FIG. 5, hemoglobin relatively strongly absorbs light having a wavelength in the region of about 400 nm to about 600 nm, compared to the infrared region. In particular, hemoglobin has a distinctively high light absorption coefficient at a wavelength of about 415 nm, which indicates a light absorption peak Hp. In the region where the wavelength exceeds 1000 nm, the light absorption coefficient of water (not shown) sharply increases. In the wavelength range of about 650 nm or more and about 1350 nm or less indicated by an open arrow indicated by a reference character W, the light absorption of hemoglobin or water is relatively low, and therefore, scattering is more likely to occur. Therefore, light in the wavelength range W indicated by the open arrow of FIG. 5 penetrates deep into a living body compared to light with the other wavelength ranges. The wavelength range W is called a "biological window." To obtain information from the inside of human biological tissue, the biological tissue is illuminated by light having a wavelength in the wavelength range W. For such purposes, incoherent light, which is less likely to cause speckle noise, has been conventionally used.

The laser light having the peak wavelength $\lambda$ has a spectral width of, for example, several nanometers. The peak wavelength $\lambda$ does not need to be equal to the wavelength of light specifically absorbed or reflected by a region of an object. For example, in the case in which the wavelength of light specifically absorbed or reflected by a region of an object is about 415 nm, the peak wavelength $\lambda$ of laser light can be, for example, 420 nm. This is because, even in such a case, that region of the object can cause absorption or reflection of laser light. The luminous efficacy perceived by the human eye is highest at about 555 nm. Therefore, a pattern of a color that is more reliably detected recognized by the human eye is observed when a speckle pattern is formed using laser light having a peak wavelength close to 555 nm than when using an absorption peak wavelength range of light absorbed by the region of an object under study. An actual color (e.g., violet) of the speckle pattern can be converted into a color (e.g., green) having a wavelength close to a wavelength (i.e., 555 nm) at which the luminous efficacy perceived by the human eye is high by image processing, and an emphasized speckle pattern can be displayed on the display device 400.

The light source device 100 according to the embodiment of the present disclosure includes the speckle variable device 12 that changes a speckle pattern shown in an image acquired by the imaging device 200 over time in response to control signals from an external device (specifically, the controller 300). The speckle variable device 12 in the present embodiment can control the formation of the speckle pattern by controlling the coherence of the laser light. Therefore, for example, the light source device 100 can be controlled to switch between an operation mode in which information is obtained from a speckle pattern, and an operation mode in which normal observation is conducted with a speckle pattern inhibited or reduced to perform ordinary observation is possible. In the operational mode in which information is obtained from the speckle pattern, the speckle variable device 12 can change the speckle pattern over time. While the speckle pattern is being changed over time, an image processing device 32 measures the change over time in the intensity signals from each pixel constituting the acquired image. The image processing device 32 can divide an imaged region of the object into a plurality of portions on the basis of a waveform of the change in the intensity signals over time. Examples of a specific constitution and operation of the speckle variable device 12 will be described below.

In this embodiment, the light source device 100 includes a white light source 14 as an irradiation light source that emits irradiation light. As used herein, "white" light widely covers light containing at least two, more preferably all, of wavelength components in the red (R), yellow (Y), green (G), and blue (B) wavelength ranges. Here, the wavelength range of the R light is, for example, from 620 nm to 660 nm. The wavelength range of the G light is, for example, from 500 nm to 540 nm. The wavelength range of the B light is, for example, from 430 nm to 480 nm. The R, G, and B light do not need to be simultaneously emitted from the white light source 14. For example, if the R light, the G light, and the B light are successively emitted within a period of about 33 milliseconds, the eye can recognize white because of additive color mixing of these color components. Y light can be emitted by exciting a phosphor with the B light. Color mixing of the B light and the Y light makes the light white. In the case in which an imaging element such as a charge-coupled device (CCD) or a complementary metal-oxide-semiconductor (CMOS) image sensor reads image data at 30 frames per second (=30 fps), the frame duration is about 33 milliseconds. Hence, if the R light, the G light, the B light, and the like are emitted successively or at the same time in one frame duration, the whitening can be achieved. Therefore, a light source that can emit the R light, the G light, the B light, and the like successively or at the same time is included in the "white light source." In the present embodiment, a typical example of the white light source 14 is a light-emitting diode (LED) or a laser diode (LD). In the case in which the white light source 14 includes an LD, the white light source 14 is constituted such that speckles are not formed as described below.

The imaging device 200 can obtain an image of the object 500 when the object 500 is illuminated by light emitted from the white light source 14. In an environment where an endoscope is used, if an irradiation light source such as the white light source 14 is not used, it is difficult to obtain a clear image of the object 500. However, the light source device 100 of the present disclosure can also be used as a light source for observing conditions of the skin or eye. In such an application, the object 500 can be illuminated by another lighting device or sunlight, and therefore, the white light source 14 is not necessary. In the environment in which an endoscope is used, the object 500 can be observed by image processing even in the case in which the object 500 is illuminated by light (preferably broadband light) that is not whitened.

In this embodiment, a superimposition of an image of the object 500, being illuminated by white light, and a speckle pattern that is formed by the laser light source 10 and the speckle variable device 12, can be displayed on the display device 400, e.g., with the speckle pattern superimposed on the image of the object 500. In the case in which a lesion may be overlooked with white light alone, the speckle pattern can prevent or reduce the oversights.

Figure 6:
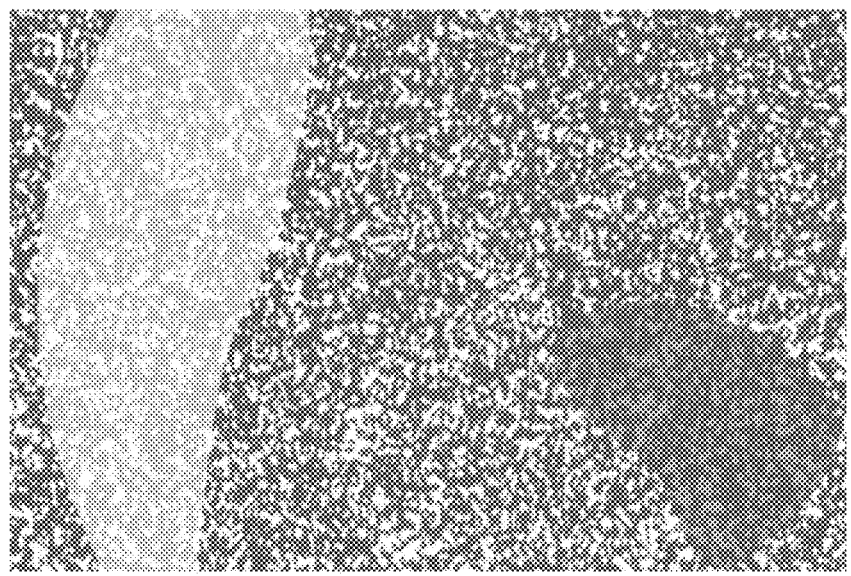
FIG. 6 shows an example image formed by superimposing an image of an object 500 that illuminated with white light on a speckle pattern formed by the laser light source 10 and a speckle variable device 12.
Figure 7:
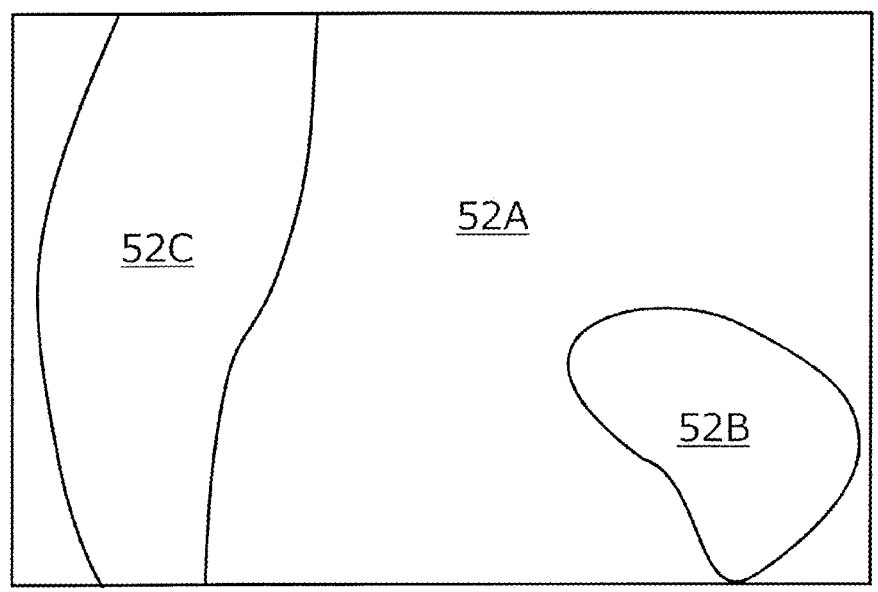
FIG. 7 is a diagram showing positions of three different regions 52A, 52B, and 52C in the image of FIG. 6.

FIG. 6 is a diagram schematically showing an example image (combined image) obtained by superimposing an image of the object 500, being illuminated by white light, and a speckle pattern formed by the laser light source 10 and the speckle variable device 12, e.g., with the speckle pattern superimposed on the image of the object 500. FIG. 7 is a diagram showing positions of three different regions 52A, 52B, and 52C in the combined image of FIG. 6. In FIG. 6, for the sake of simplicity, a detailed structure of the image of the object 500 being illuminated by white light is not shown, and only the speckle pattern is shown. The regions 52A, 52B, and 52C can be distinguished from each other based on features (e.g., brightness and contrast, etc.) of the speckle pattern. In the example of FIG. 6, the region 52B absorbs laser light having the wavelength $\lambda$ more strongly than does the region 52A. Therefore, the brightness of speckles is generally lower in the region 52B than in the region 52A. In contrast to this, the region 52C reflects laser light having the wavelength $\lambda$ more strongly than does the region 52A. Therefore, the brightness of speckles is higher in the region 52C than in the region 52A as a whole. A reason why regions can be distinguished from each other based on a speckle pattern is that the peak wavelength $\lambda$ of laser light emitted from the laser light source 10 is in the wavelength range of light that is specifically absorbed or reflected by the regions 52B, 52C of the object 500, and the coherence of laser light is maintained high. If the object 500 is illuminated only by light emitted from the white light source 14, the speckle pattern of FIG. 6 is not observed, and therefore, it may be difficult to classify the regions 52A, 52B, and 52C.

In the case in which the peak wavelength $\lambda$ of laser light is about 415 nm, the region 52B may contain, for example, a larger amount of blood components including hemoglobin than those of the other regions. Red blood cells, which contain hemoglobin, can inherently scatter laser light, and therefore, contribute to formation of a speckle pattern. However, in the case in which laser light is strongly absorbed by hemoglobin, the intensity of scattered light decreases, and therefore, the intensity (brightness) of speckles also decreases. In the case in which the blood containing red blood cells is flowing in a blood vessel, the phase of scattered light by red blood cells changes over time. Therefore, the time-averaged contrast of speckles decreases.

The distinguishing of the regions based on the speckle pattern contributes to detection of a region having an abnormality such as a lesion in biological tissue. In the present embodiment, identification of the regions based on the speckle pattern is performed using the image processing device 32 shown in FIG. 4. With various features extracted from the speckle pattern that changes over time as described below, a region can be segmented or classified based on these features.

In the case in which only illumination by a normal white light source is performed, a clear contrast difference may not occur between a lesion and a surrounding portion of biological tissue, and therefore, it may be difficult to classify the lesion in an image. In such a case, by using the speckle pattern as described above, the occurrence of overlooking can be prevented or reduced. Therefore, the light source device of this embodiment can exhibit a particularly good effect as a light source for an endoscope.

Figure 8:
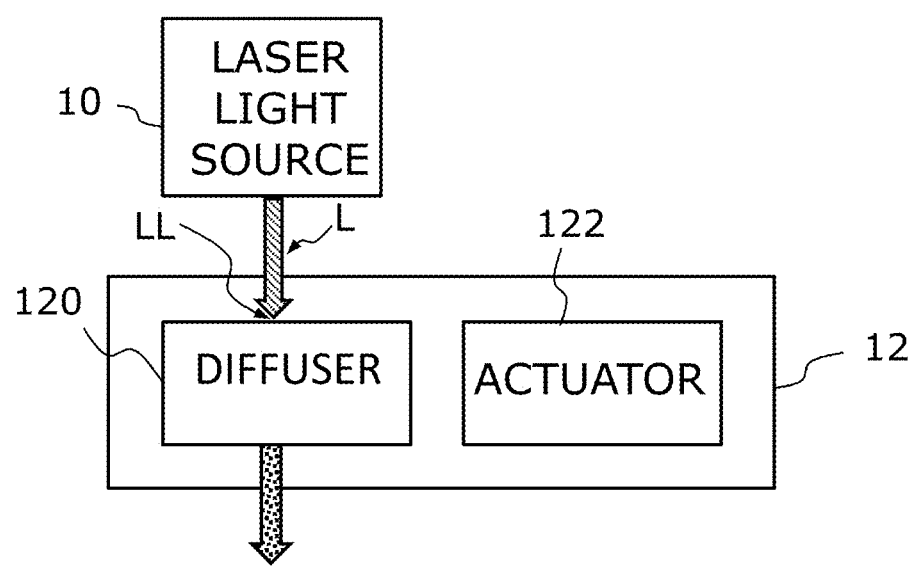
FIG. 8 is a block diagram showing an example configuration of the speckle variable device 12.

FIG. 8 is a block diagram showing an example basic configuration of the speckle variable device 12. The speckle variable device 12 of this example includes a diffuser 120, and an actuator 122 that moves (transfers) the diffuser 120. The movement of the diffuser 120 includes rotation, wobbling, and/or vibration. The actuator 122 is configured to change a moving condition such as a velocity or vibration frequency of the diffuser 120, and stop the diffuser 120. The diffuser 120 is disposed on an optical path of the laser light L emitted from the laser light source 10, to scatter the laser light L. The actuator 122 can move the diffuser 120 so that an incident position LL of the laser light L on the diffuser 120 changes as elapse of time. The actuator 122 can provide a variable speckle contrast by temporally and spatially changing the coherence of the laser light L which is transmitted through or reflected by the diffuser 120.

Figure 9A:
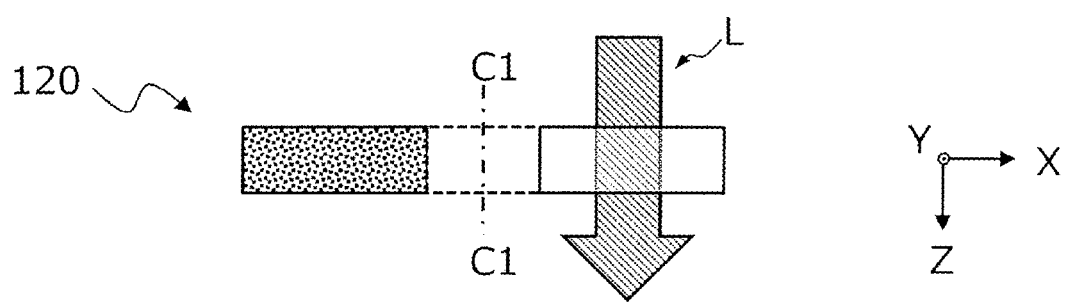
FIG. 9A is a schematic cross-sectional view of a diffuser 120 according to one embodiment of the present disclosure.
Figure 9B:
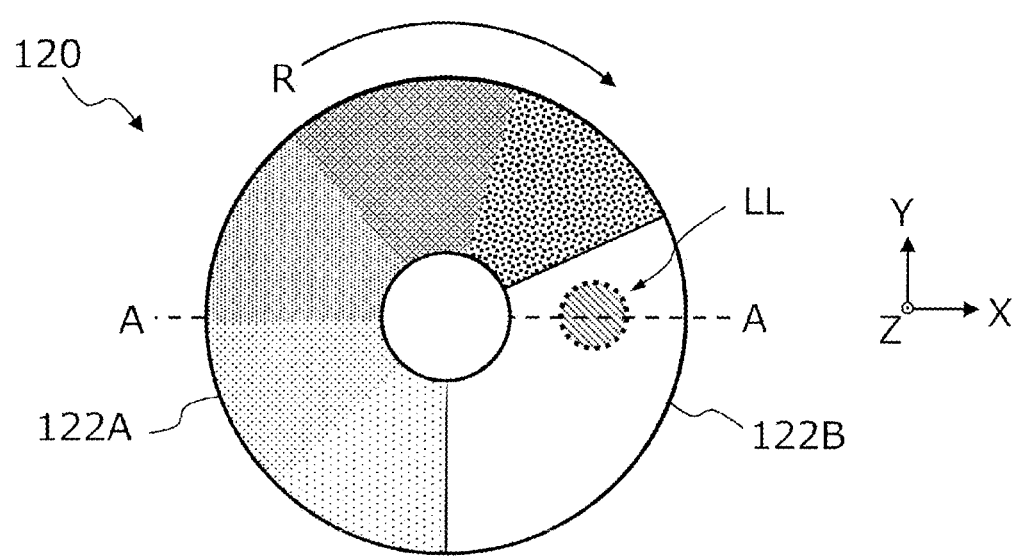
FIG. 9B is a schematic plan view of the diffuser 120.

FIG. 9A is a schematic cross-sectional view of the diffuser 120 in this embodiment. FIG. 9B is a plan view of the diffuser 120 in this embodiment. The cross-section of FIG. 9A is an illustration taken along line A-A of FIG. 9B.

The diffuser 120 of FIGS. 9A and 9B, which is in the shape of a disc, is supported such that the diffuser 120 can be rotated about a central axis C1. The diffuser 120 can be rotated in a direction indicated by an arrow R or in a direction opposite to the direction indicated by the arrow R. In order to exhibit light scattering capability, the diffuser 120 can contain a large number of particles for scattering (e.g., scattering particles) on a surface or inside the diffusing element, or alternatively, the diffuser 120 can have a so that the optical thickness thereof varies from position to position. In order to allow the diffusing element 120 to strongly scatter the laser light L, it is preferable that a plurality of scattering particles or fine surface roughness exist in a region of the diffuser 120 where the laser light L is incident, that is, a cross-section of the laser light L. Although the diffuser 120 of FIGS. 9A and 9B is of the transmission type, the diffuser 120 can be of the reflection type.

The diffuser 120 of this embodiment has light scattering capability that varies from position to position or from region to region. Specifically, the diffuser 120 has, for example, a structure that the degree of scattering changes continuously or discontinuously in the circumferential direction around the central axis C1. Because the diffuser 120 has light scattering capability that varies from position to position or from region to region, instead of uniform light scattering capability, the coherence of the laser light L that is transmitted through or reflected by the diffuser 120 can be readily changed. The coherence can also be controlled by adjusting the rotational speed (movement speed) of the diffuser 120.

In the case in which the diffuser 120 contains scattering particles, any of the size, shape, and particle number density of the scattering particles can be changed, depending on position or region on the diffuser 120. Alternatively, the optical thickness of the diffuser 120 can be changed, depending on position or region. The optical thickness can be changed by, for example, forming fine roughness on at least one of the front and back surfaces of the diffuser 120.

The laser light L transmitted through or reflected by a region having light scattering capability has a random phase distribution due to scattering. However, when the diffuser 120 is at rest, the random phase distribution does not change over time, and therefore, the coherence is maintained. In other words, similarly to the formation of a speckle pattern by random phase distribution of laser light scattered by the scattering portion of the object, the laser light L scattered by the diffusing element 120 also forms a speckle pattern. When the laser light L forming such a speckle pattern is incident on the object 500 (FIG. 4), the object 500 also causes scattering, and therefore, the two respective speckle patterns caused by scattering of the diffuser 120 and the object 500 are superimposed to form a new speckle pattern. The contrast of the speckle pattern cannot be changed in this state. In order to provide a variable speckle contrast, the diffuser 120 may need to be moved so as to change the speckle pattern of the laser light L scattered by the diffuser 120. Temporally and spatially superimposing a plurality of speckle patterns having no correlation with each other in this manner can averaging the intensity of the laser light L and decrease the contrast of the speckle pattern.

A speckle pattern can be also intentionally formed. To this end, the diffuser 120 is stopped. When laser light is transmitted through or reflected by the stopped diffuser 120, the laser light L may be scattered. Such scattering by the diffuser 120 can allow the laser light L illuminating the object 500 to form a speckle pattern as described above. Superimposition of such speckle patterns can further increase contrast, which contributes to distinguishing a lesion.

The diffuser 120 can include a scattering material region 122A that causes scattering, and in addition, a transparent portion 122B that does not cause scattering. In the case in which the laser light L emitted from the laser light source 10 is transmitted through the transparent portion 122B of the stopped diffuser 120, scattering does not occur, and therefore, the decrease in the intensity of the laser light L can be prevented or reduced. When the laser light L passes through the transparent portion 122B, the diffuser 120 does not need to be stopped, and can be vibrating or moving at a sufficiently low speed.

According to the embodiment of the present disclosure, an observer of an object can increase or decrease speckle contrast as appropriate while visually checking the image displayed on the display device 400 of FIG. 4. Specifically, an observer of the object 500 that is shown in FIG. 4, or an operator of the image-capturing device 1000, can control the operation of the speckle variable device 12 by operating the controller 300 using an input device (not shown). For example, an image of the object 500 is initially observed without a speckle pattern formed, and a speckle pattern can be superimposed, as appropriate, on a normal image of the object.

In the case in which the rotating diffuser 120 as shown in FIGS. 9A and 9B is used, the diffuser 120 is rotated at a high speed in an observation mode that a speckle pattern is not formed. On the other hands, in an observation mode that a speckle pattern is formed, the diffuser 120 is rotated at a low speed or is stopped. Desirably, the stopping is achieved by accurately controlling the rotational position (or angular position) of the diffusing element 120 such that the laser light L passes through the transparent portion 122B of the diffusing element 120. Such a rotating operation can be performed using a brushless DC motor, stepping motor, or the like as the actuator 122. The angular position of the diffuser 120 can be controlled using, for example, a device that detects or estimates the angular position of rotation in combination with the motor.

The number of diffusers 120 disposed on the optical path of the laser light L is not limited to one. A plurality of diffusers 120 can be disposed on the optical path. The plurality of diffusers 120 can, for example, include a rotating diffuser and a static diffuser. The configuration of the diffuser 120 is not limited to the example of FIGS. 9A and 9B, and the diffuser 120 can have various configurations. The actuator 122 can wobble or vibrate the diffuser 120 instead of rotating the diffuser 120.

Figure 10:
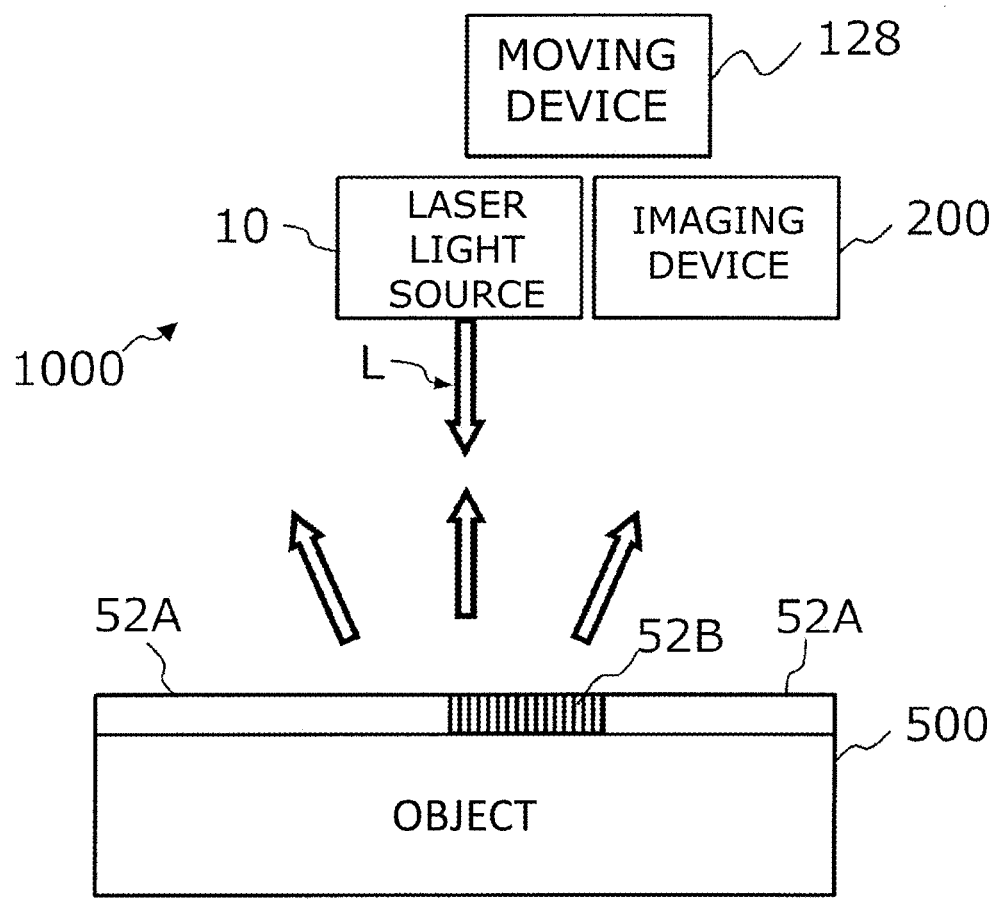
FIG. 10 is a diagram schematically showing the relative positional relation of the light source device 100 and an imaging device 200 with respect to the object 500, and shows a moving device 128 that changes their positions.

The speckle variable device 12 can change the speckle pattern over time by changing the incidence angle of the laser light L on the object 500 or changing the distance from the position of emission of the laser light L to the object 500. When the objective speckle pattern is formed in three-dimensional space by scattering the coherent laser light L at the object 500, the speckle pattern depends on not only the coherence of the laser light L but also the relative positional relation (e.g., position and orientation) between the light source device 100 and the object 500. The subjective speckle pattern observed with the imaging device 200 also depends on the positional relation (e.g., position and orientation) between the imaging device 200 and the object 500. Therefore, the speckle pattern to be observed can be changed over time also by, for example, changing the position or orientation of at least one of the light source device 100 and the imaging device 200 relative to the object 500 over time while retaining the moving state or the stopped state of the diffuser 120. FIG. 10 schematically shows a moving device 128 that changes the relative positional relation of the light source device 100 and the imaging device 200 relative to the object 500. The moving device 128 can be, for example, a movable mechanism that bends the distal portion of an endoscope.

The speckle variable device 12 is not limited to a device in which the diffuser is installed. Examples of the speckle variable device 12 includes a mechanism that changes the position or orientation of at least one of the light source device 100 and the imaging device 200 relative to the object 500 over time, as described above.

Figure 11:
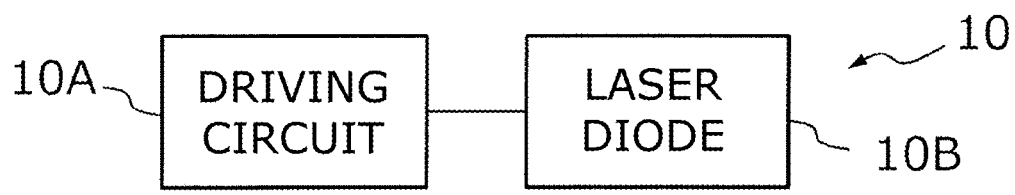
FIG. 11 is a block diagram schematically showing a laser diode 10B and a driving circuit 10A according to one embodiment of the present disclosure.
Figure 12:
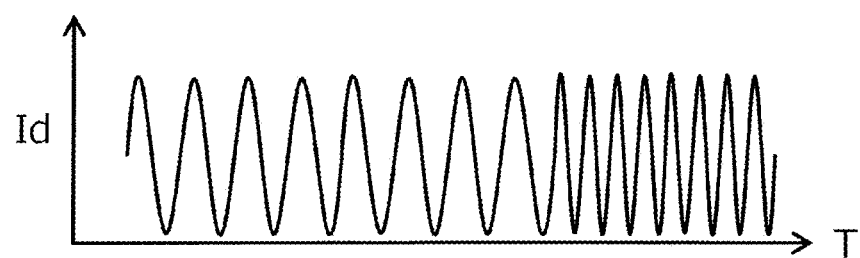
FIG. 12 is a diagram showing an example of modulation of a current waveform supplied from the driving circuit 10A to the laser diode 10B.

An example of the speckle variable device 12 includes a driving circuit 10A supplying a current, on which a high-frequency current has been superimposed, to a laser diode 10B in the laser light source 10 as shown in FIG. 11. FIG. 12 schematically shows an example of modulation of a current waveform supplied from the driving circuit 10A to the laser diode 10B. In FIG. 12, the vertical axis shows drive current Id, and the horizontal axis shows time T. The driving circuit 10A can broaden or narrow the width of the lasing wavelengths of the laser light L emitted from the laser diode 10B by such modulation of the drive current Id. The coherence of the laser light L can vary according to the width of the lasing wavelengths. The driving circuit 10A can change the speckle pattern over time by changing the amplitude or frequency of the high-frequency current to be superimposed over time. If the currents are superimposed so as to oscillate around the threshold current of the laser diode, relaxation oscillation is induced, to thereby further improving this effect.

Next, an example image signal obtained by the imaging device 200 will be described. As shown in FIG. 1, the imaging device 200 includes the imaging optical system 20 and the imaging element 22.

Figure 13A:
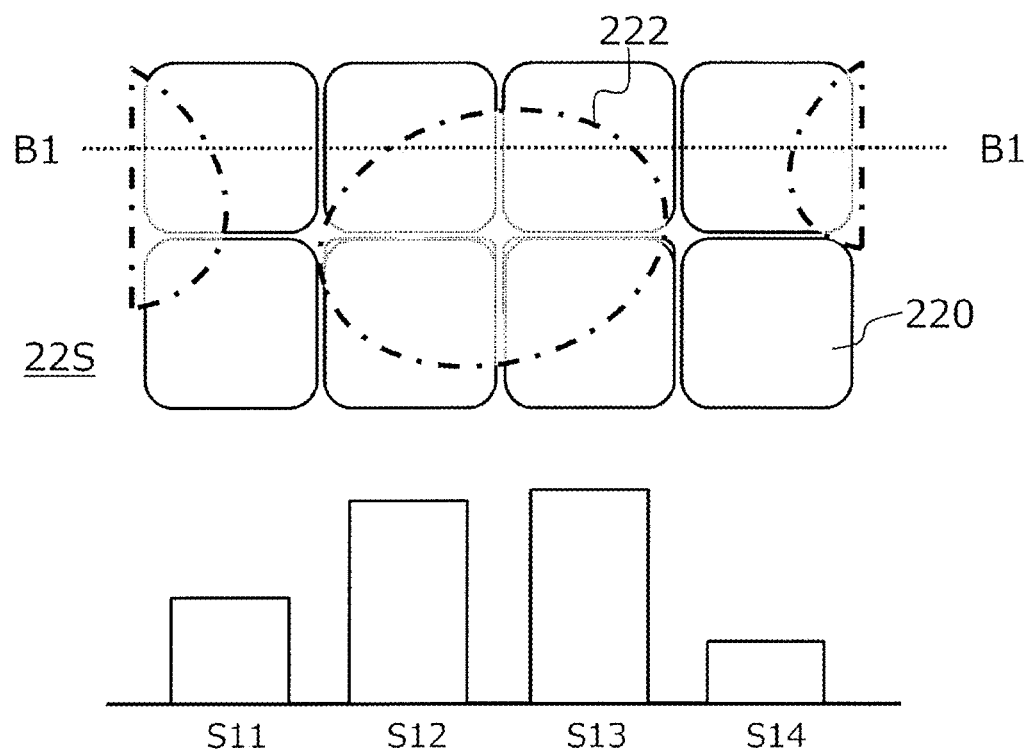
FIG. 13A is a diagram schematically showing a portion of an array of pixels 220 on the imaging surface 22S of an imaging element 22 and signals obtained from several pixels 220.

FIG. 13A is a diagram showing a portion of an array of pixels 220 on the imaging surface 22S of the imaging element 22, and signals obtained from several pixels 220. Each pixel 220 has a photoelectric conversion section that outputs an electrical signal depending on the amount of incident light. Each pixel 220 is connected to a read circuit, etc., through a wiring (not shown). An upper portion of FIG. 13A schematically shows eight pixels 220 arranged in a matrix of four rows and two columns, and speckles 222 formed on the imaging surface 22S. In a lower portion of FIG. 13A, the intensity of signals S11, S12, S13, and S14 respectively outputting from four pixels 220 taken along the line B1-B1 in the upper side is schematically shown as the heights of respective bars.

As can be seen from FIG. 13A, the pixels 220 are smaller than the speckles 222 in this example. If the pixels 220 are larger than the speckles 222, it is difficult to clearly observe a speckle pattern. When a speckle pattern is stationary, the intensity of a signal output from each pixel 220 is temporally constant.

Figure 13B:
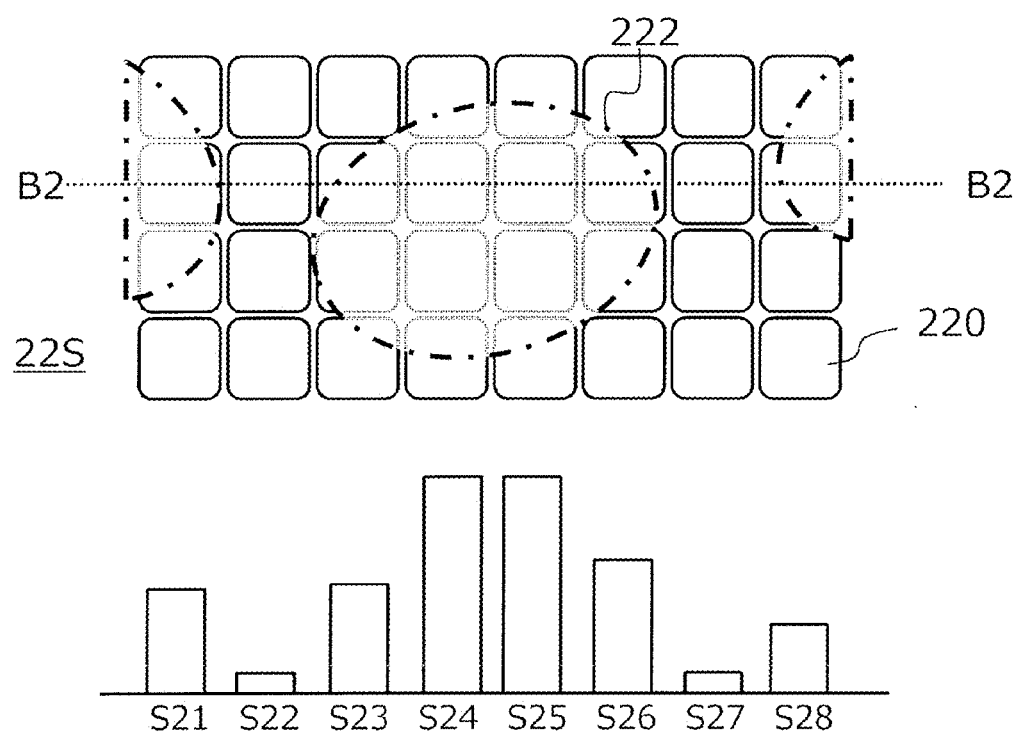
FIG. 13B is a diagram schematically showing a portion of another array of pixels 220 on the imaging surface 22S of the imaging element 22 and signals obtained from several pixels 220.

FIG. 13B shows an example in which the size and array pitch of each pixel 220 are smaller than those in the example of FIG. 13A. The upper portion of FIG. 13B schematically shows 32 pixels 220 arranged in a matrix of eight rows and four columns, and speckles 222 formed on the imaging surface 22S. In the lower portion of FIG. 13B, signals S21, S22, S23, S24, S25, S26, S27, and S28 respectively outputting from eight pixels 220 taken along the line B2-B2 in the upper side are schematically shown as the heights of respective bars.

As can be seen from FIGS. 13A and 13B, the smaller the size and arrangement pitch of the pixels 220 are, the higher the degree of definition of the speckle pattern to be observed becomes. In order to allow a speckle pattern formed by laser light having a peak wavelength $\lambda$ to be observed, the pixel 220 may need to perform photoelectric conversion in response to the light having the wavelength $\lambda$. In the case in which the imaging device 200 is a color image sensor, each pixel 220 of FIGS. 13A and 13B includes, for example, an R subpixel, a G subpixel, and a B subpixel. These subpixels are arranged, for example, in a Bayer pattern in each pixel 220. In that case, an image signal includes a signal component of each of R, G, and B. In the case in which the peak wavelength of laser light is, for example, about 415 nm, a bright portion of a speckle pattern can be detected by the B subpixel.

The imaging element (e.g., image sensor) used in the imaging device 200 can read a pixel signal on a frame-by-frame basis. In the case in which the readout rate is, for example, 30 frames per second, the duration of each frame is about 30 milliseconds. In that case, a pixel signal is read about every 30 milliseconds. A pixel signal obtained from a pixel 220 has an intensity corresponding to the amount of electric charge accumulated in the pixel 220 by photoelectric conversion in the duration of exposure, which is shorter than the duration of a frame. Therefore, if speckles are moved over a distance that is longer than the pixel size in the exposure duration, it is difficult to clearly detect a speckle pattern. Therefore, in the mode that a speckle pattern is observed, it is desirable that the speckle pattern be not moved at high speed. A speckle pattern is changed when the light source device 100 and the imaging device 200 are moved with respect to the object 500 of FIG. 4. The speckle pattern can be changed also by changing the coherence of the laser light L emitted from the light source device 100 over time by, for example, rotating the diffusing element 120. Therefore, in order to obtain a static speckle pattern, it is desirable to substantially stop the light source device 100 and the imaging device 200 with respect to the object 500, and illuminate the object 500 by highly coherent laser light L from the light source device 100.

The "speckle contrast" is known as a quantity (statics) for statistically evaluating a speckle pattern. The "speckle contrast" is defined by the following equation:

$$C = \sigma/J \quad \text{(Equation 1)}$$

where C represents the speckle contrast, J represents the spatial average value of light intensity, and σ represents the standard deviation of light intensity.

A spatial distribution of "light intensity" on the imaging surface 22S can be measured from the intensities of signals output from the pixels 220 of FIGS. 13A and 13B. As a result, J and σ can be calculated.

Figure 14:
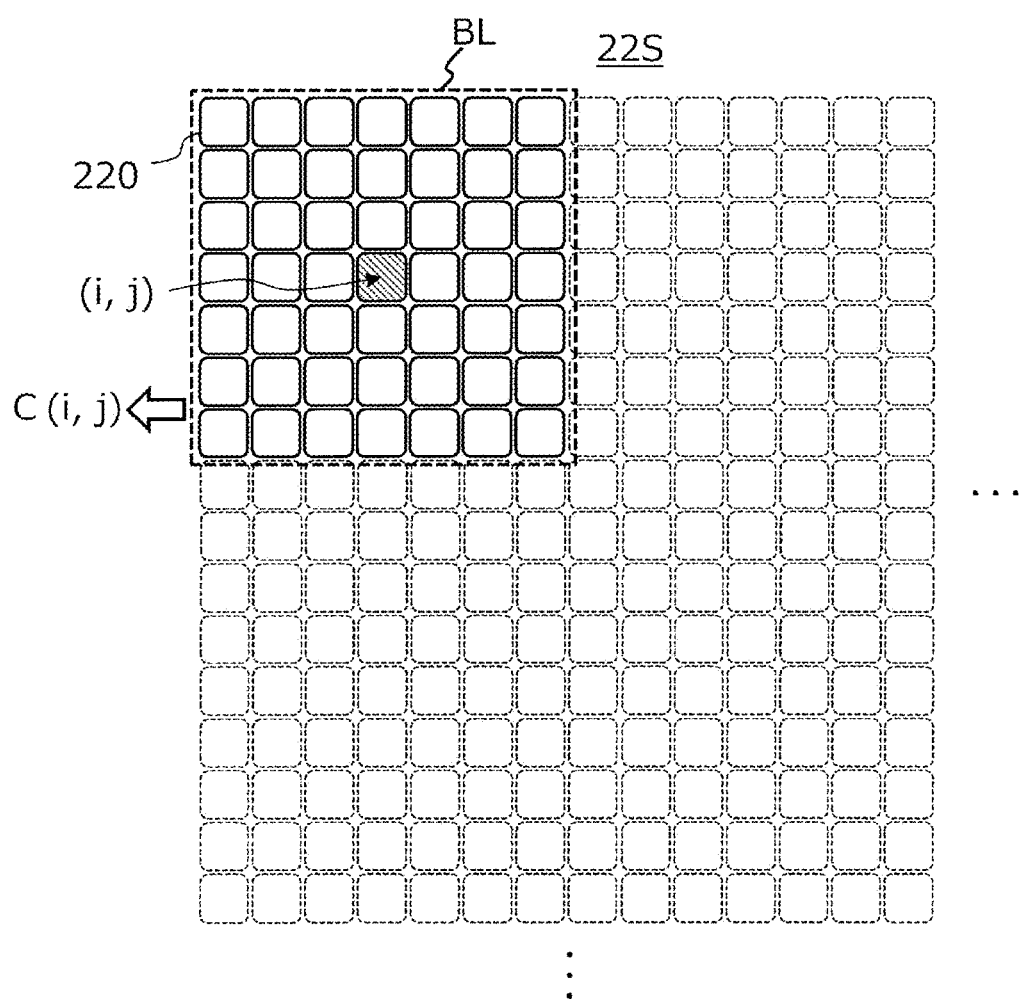
FIG. 14 is a diagram schematically showing an example of a portion of an array of pixels 220 on the imaging surface 22S, and the bounds of a pixel block.

An example calculation of a speckle contrast from a plurality of pixels on a block-by-block basis will be described with reference to FIG. 14. FIG. 14 is a diagram schematically showing an example of a portion of an array of pixels 220 and a pixel block on the imaging surface 22S.

In the example of FIG. 14, the speckle contrast C of a pixel (i, j) at a position (i, j) on the imaging surface 22S can be determined based on, for example, pixel signals obtained from a block BL of 7×7 pixels containing the pixel (i, j) as the center thereof. Specifically, C(i, j) can be obtained by calculating the average value J and the standard deviation σ from signals from all pixels in the pixel block BL. The number of pixels in the pixel block BL is not limited to 7×7, and can be 9×9 or other sizes. The two-dimensional array of C(i, j), that is, the contrast image, can be obtained by calculating C(i, j) for all pixels while sliding the pixel block BL so that the central pixel (i, j) of interest is shifted pixel-by-pixel in the row or column direction. In the case in which each pixel is sufficiently smaller than a speckle, C(i, j) can be calculated after substantially reducing the pixel density by adding signals from several adjacent pixels. Such C(i, j) can be called a "local speckle contrast." The local speckle contrast can serve as a feature, which is measurable property or characteristic of a region of interest in the speckle pattern, for distinguishing a lesion from other portions. The speckle contrast can be calculated by the image processing device (computation circuit) 32 shown in FIG. 4. The image processing device 32 operates together with a processor 30 to generate image data based on an image signal obtained from the imaging device 200. The image data in this manner generated can be displayed on the display device 400.

When the speckle pattern is at rest, the intensities of the signals output from individual pixels 220 do not change over time. When the speckle pattern is being changed over time by the function of the speckle variable device 12, the intensities of the signals output from individual pixels 220 change over time.

Figure 15A:
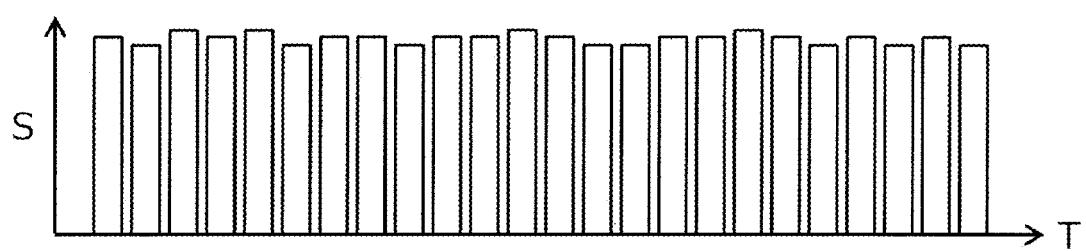
FIG. 15A is a diagram showing an example of signals output from a pixel $(i_a, j_a)$ on the imaging surface 22S.
Figure 15B:
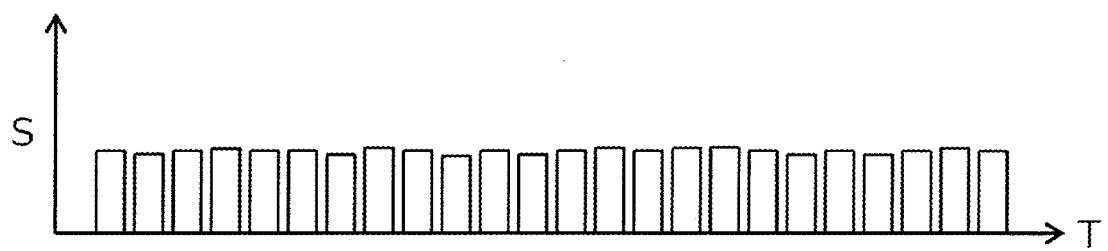
FIG. 15B is a diagram showing an example of signals output from a pixel $(i_b, j_b)$ on the imaging surface 22S.

FIG. 15A and FIG. 15B schematically show respective examples of the signals output from a pixel $(i_a, j_a)$ at a position $(i_a, j_a)$ and the signals output from a pixel $(i_b, j_b)$ at a position $(i_b, j_b)$ on the imaging surface 22S. In each drawing, the vertical axis shows signal intensity, and the horizontal axis shows time. As described above, in the case in which the readout rate is, for example, 30 fps, the signals are read about every 33 milliseconds. FIG. 15A and FIG. 15B each schematically show signals of 24 frames (about 0.8 seconds). In this example, the speckle pattern hardly changes in 0.8 seconds, but the signal intensity of the pixel $(i_b, j_b)$ is relatively smaller than the signal intensity of the pixel $(i_a, j_a)$. This may be because a dark portion of the speckle pattern is located in a region of the object 500 corresponding the pixel $(i_b, j_b)$, or because the region of the object 500 has the property of absorbing the laser light. It is difficult to sort the regions of the object 500 by the properties on the basis of the static signals output from individual pixels.

Figure 16A:
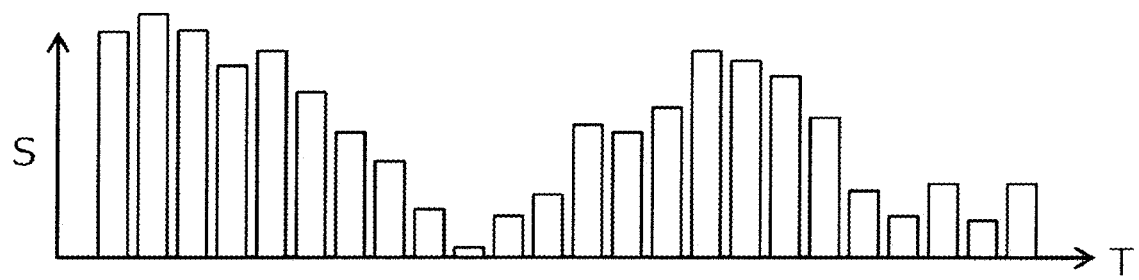
FIG. 16A is a diagram showing an example of signals output from the pixel $(i_a, j_a)$ in the case in which the speckle pattern is changed by the function of the speckle variable device 12.
Figure 16B:
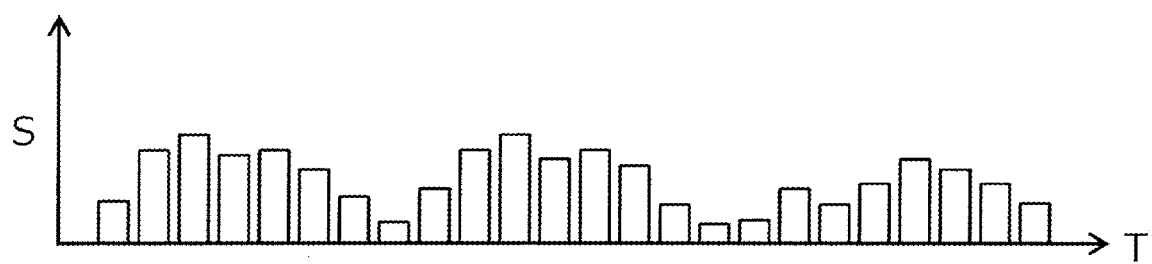
FIG. 16B is a diagram showing an example of signals output from the pixel $(i_b, j_b)$ in the case in which the speckle pattern is changed by the function of the speckle variable device 12.

FIG. 16A and FIG. 16B schematically show respective examples of signals output from the pixel $(i_a, j_a)$ and the pixel $(i_b, j_b)$ in the case in which the speckle pattern is changed by the function of the speckle variable device 12. The signals output from the pixel $(i_a, j_a)$ and the pixel $(i_b, j_b)$ have different waveforms according to change in the speckle pattern over time. In the examples in FIG. 16A and FIG. 16B, the fluctuation amplitude (variation) of the signals output from the pixel $(i_b, j_b)$ is smaller than the fluctuation amplitude of the signals output from the pixel $(i_a, j_a)$. This is because the region of the object 500 corresponding to the pixel $(i_b, j_b)$ has the property of absorbing the laser light. The "fluctuation amplitude" can be determined by subtracting the "minimum value of the signals" from the "maximum value of the signals" measured in a predetermined period (such as one second). The region with a smaller "fluctuation amplitude" than other regions is recognized as a region that is more likely to absorb (i.e., less likely to scatter) the laser light than other regions. For example, in the case in which a speckle pattern is formed using laser light with a peak wavelength of about 415 nm, a fluctuation amplitude smaller than the fluctuation amplitudes of other regions is observed in a bleeding portion of the object.

The difference in absorption or reflection properties of light can be quantitatively detected for each region of the object by changing the speckle pattern over time using the speckle variable device 12 as described above. More specifically, for example, the fluctuation amplitude is determined for every a single or a plurality of pixels, and a single or a plurality of pixels can be identified or sorted into a plurality of regions according to the magnitude of the fluctuation amplitude. For example, using the laser light with the peak wavelength of 415 nm enables sort of the pixel(s) into regions with high, low, and intermediate light absorptances at this wavelength on the basis of the fluctuation amplitude. Division or identification of the regions of the object can be performed by the image processing device (computation circuit) 32 without being based on the personal opinion of the observer. The image of the object divided into the plurality of portions, or classified regions, can be displayed on the display device 400 in FIG. 4. At the time of displaying, the color or lightness can be changed for emphasis. For example, emphatically displaying a region including a pixel or a group of pixels with a lower (or higher) fluctuation amplitude than the fluctuation amplitudes of other regions contribute to reduction or prevention of oversights of lesions in the image of the object.

In the case in which the imaging device 200 is a color image sensor and in which each pixel includes the R subpixel, the G subpixel, and the B subpixel, the pixel refers to the subpixel having detection sensitivity to a color covering the peak wavelength of the laser light. Intensity signals that vary in response to change in the speckle pattern over time are not acquired from a subpixel that does not have detection sensitivity to the color covering the peak wavelength of the laser light. Therefore, the image processing device 32 can select the signals output from at least one subpixel of a single color or a plurality of colors including a subpixel of the color in the wavelength range covering the peak wavelength of the laser light from among the R subpixel, the G subpixel, and the B subpixel as the intensity signals of each pixel.

In the present embodiment, quantitative evaluation based on features such as fluctuation amplitudes acquired by the image processing device 32 facilitates detection of a lesion or the like, even in the case in which it is difficult to detect the difference in speckle patterns by human eyes. In the case in which the speckle pattern is formed using the laser light with a peak wavelength of about 415 nm as described above, for example, the speckle contrast to be observed can vary according to the blood flow velocity in a portion such as the inside of the blood vessel through which blood is flowing. Accordingly, measuring both of the fluctuation amplitude and the speckle contrast while changing the speckle pattern over time can increase information to be acquired from the object, so that a narrowed or bleeding region of the blood vessel can be detected with less oversights.

Various features can be extracted from the waveform of the intensity signals (speckle signals) acquired from each pixel of the imaging device 200 while the speckle pattern is changed over time by the speckle variable device 12. Division or sorting of the regions based on such features can also be performed using a pre-trained model created by machine learning such as deep learning. Using machine learning may enable "machine" segmentation of the regions, and therefore diagnosis of lesions without the help of human vision and experience.

As described above, the minimum size of a speckle on the imaging surface 22S depends on the numerical aperture NA of the imaging optical system 20 in the imaging device 200 and the wavelength λ of the laser light L. More accurately, the minimum size of a speckle on the imaging surface 22S is represented by 2.44×λ(1+M)×f-number, where M represents a lateral magnification (or image magnification) by the imaging optical system 20, and f-number, also referred to as a "focal ratio," is equal to 2/NA. The value (1+M)×f-number is called an "effective f-number." It the lateral magnification M is in an appropriate range taking into consideration the size and array pitch, etc., of the pixels 220 on the imaging surface 22S, speckles having a size suitable for detection of a specific type of lesion can be formed on the imaging surface 22S.

The feature of a speckle pattern is not limited to a speckle contrast, and can be a signal/noise ratio (SN ratio). The average size, number density, or the like of speckles can be calculated by image processing, and these can be employed as a feature of a speckle pattern.

Next, an embodiment in which the light source device 100 is used as a light source for an endoscope will be described with reference to FIG. 17.

Figure 17:
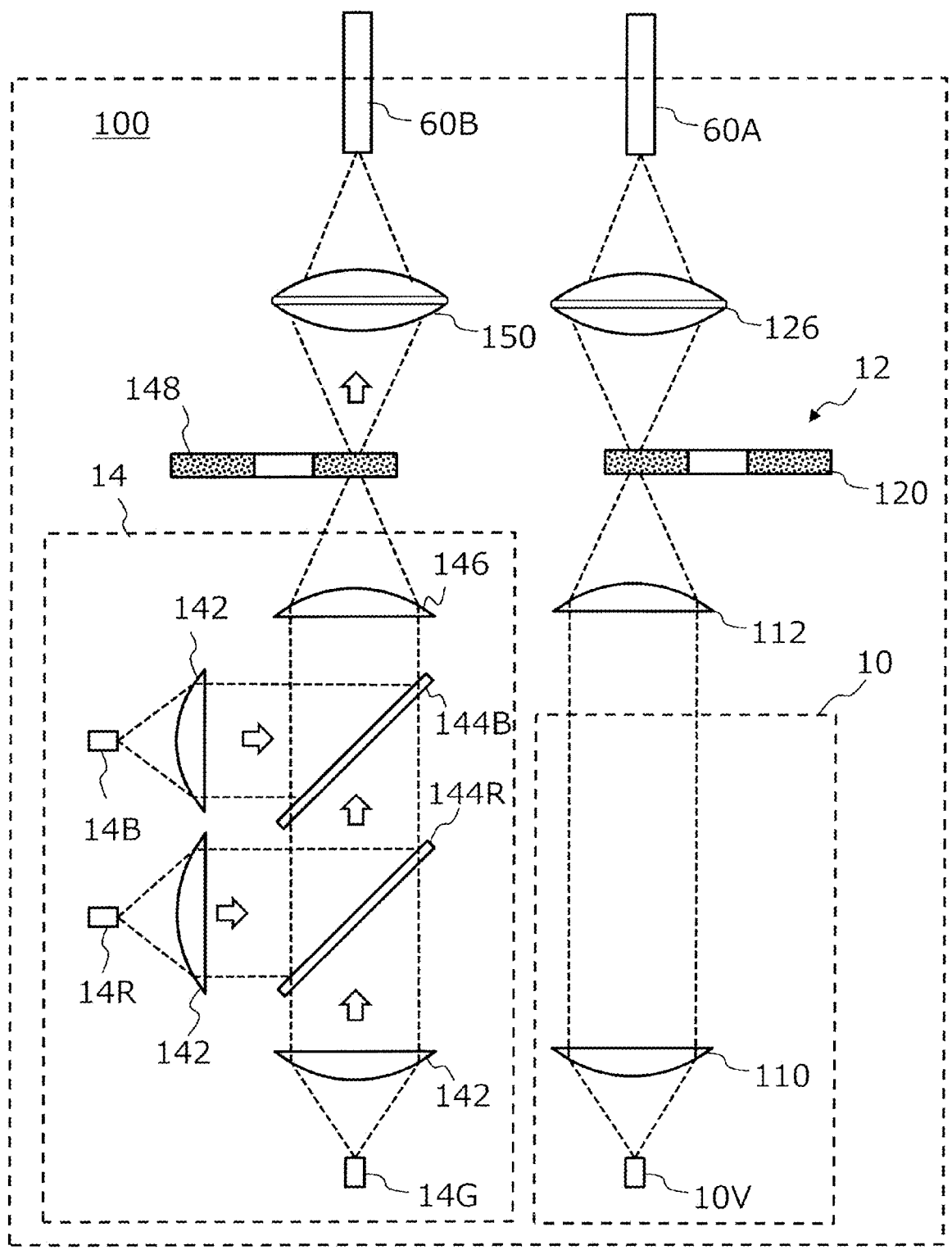
FIG. 17 is a diagram schematically showing an example configuration of a light source device in which white light and laser light can be coupled to optical waveguides, such as an optical fiber.

FIG. 17 is a diagram schematically showing an example configuration of the light source device 100 in which white light and laser light can be coupled to an optical waveguide, such as an optical fiber. The light source device 100 of FIG. 17 has a condenser lens 126 that optically couples laser light whose coherence is controlled by the speckle variable device 12 to an optical waveguide 60A of an endoscope. The specific constitution of the endoscope can be selected as appropriate. The endoscope is not limited to a flexible endoscope, and can be a rigid endoscope.

The light source device 100 will now be described in detail. The light source device 100 of FIG. 17 includes a laser light source 10, a speckle variable device 12, and a white light source 14.

The laser light source 10 includes, for example, a blue-violet laser diode (LD) 10V having a peak wavelength λ of 415 nm. Laser light emitted from the blue-violet LD 10V is collimated by a lens 110, and thereafter, is converged by a condenser lens 112 on the diffuser 120 of the speckle variable device 12. The laser light transmitted through the diffuser 120 is converged on an end surface on the incident side of the optical waveguide 60A by the condenser lens 126, and is optically coupled to the optical waveguide 60A, such as an optical fiber. The laser light propagating in the optical waveguide 60A is then emitted from a distal portion of the endoscope, and illuminate an object that is biological tissue. In the mode for intentionally observing a speckle pattern, the coherence of laser light transmitted through the speckle variable device 12 is not reduced, and therefore, a speckle pattern having high contrast can be observed. In the mode that observation of a speckle pattern is inhibited or suppressed, the coherence of laser light transmitted through the speckle variable device 12 is reduced, and therefore, speckle pattern is hardly observed. In either observation modes, an object under study can be illuminated by white light emitted from the white light source 14.

In the example of FIG. 17, the white light source 14 includes a red LD 14R, a green LD 14G, and a blue LD 14B. Laser light beams emitted from the LDs 14R, 14G, and 14B are collimated by respective lenses 142. Laser light emitted from the red LD 14R is collimated, and thereafter, is reflected by a dichroic mirror 144R, next passes through a dichroic mirror 144B, and enters a condenser lens 146. Laser light emitted from the green LD 14G is collimated, and thereafter, passes through the dichroic mirror 144R and the dichroic mirror 144B, and enters the condenser lens 146. Laser light emitted from the blue LD 14B is collimated, and thereafter, is reflected by the dichroic mirror 144B, and enters the condenser lens 146. Thus, the laser light beams emitted from the LDs 14R, 14G, and 14B are converged on a rotating diffuser 148 by the condenser lens 146. The rotating diffuser 148 reduces the coherence of the laser light to a level at which speckles are not formed. The diffuser 148 does not need to have a special configuration that light scattering capability varies from position to position, unlike the diffuser 120 of the speckle variable device 12. The diffuser 148 is driven by a motor to rotate at, for example, 3600 or more revolutions per minute. Laser light transmitted through the rotating diffuser 148 is converged on an end surface on an incident side of an optical waveguide 60B such as an optical fiber and is optically coupled to the optical waveguide 60B. The laser light (white light) propagating in the optical waveguide 60B is then emitted from the distal portion of the endoscope, and illuminates an object that is biological tissue.

The optical waveguides 60A and 60B can be connected to a light guide or optical fiber cable in the endoscope through a beam combiner (e.g., wave-combining device) (not shown). Such a beam combiner can be incorporated in the light source device 100.

In the example of FIG. 17, the three primary color components constituting white light are each laser light emitted from a laser diode (LD). The configuration of the white light source in the embodiment of the present disclosure is not limited to this example. All or a portion of the three primary color components constituting white light can be light emitted from an LED, or light emitted from a lamp, such as a tungsten lamp. Light emitted from an LED or lamp is incoherent, and therefore, the rotating diffuser 148 is unnecessary. Alternatively, white light can be produced by exciting a phosphor with laser light emitted from a blue laser diode or ultraviolet laser diode. Fluorescent light produced by a phosphor is incoherent. In the case in which white light is produced by exciting a phosphor by ultraviolet laser light, all visible light components are provided by fluorescent light, and therefore, the rotating diffuser 148 is unnecessary. Also in the case in which a phosphor is excited with blue laser light, the rotatable diffusing element 148 does not necessarily have to be used because the laser light is scattered while passing through the phosphor and mixed with fluorescence of a yellow color component.

Next, an example configuration of an image-capturing device applied to an endoscope will be described with reference to FIG. 18.

Figure 18:
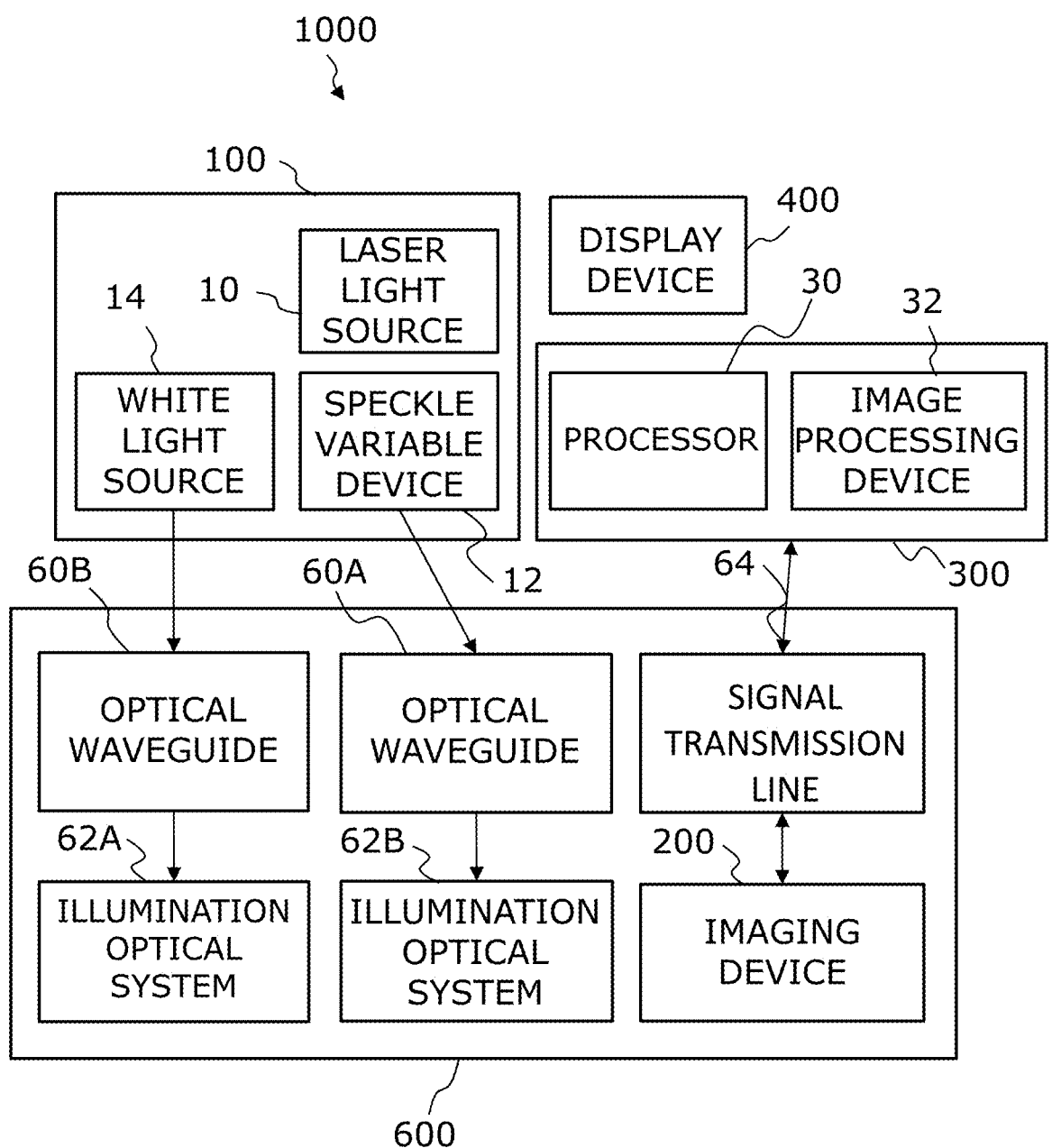
FIG. 18 is a diagram showing an example configuration of an image-capturing device including an endoscope.

An image-capturing device 1000 shown in FIG. 18 includes a light source device 100, an imaging device 200, and a controller 300 that is configured to control operations of the light source device 100 and the imaging device 200. The controller 300 includes a processor 30 and an image processing device 32, and is connected to a display device 400. The configuration of the light source device 100 can be similar to that described above with reference to FIG. 17, for example. The processor 30 is typically a microcontroller including a semiconductor integrated circuit. A memory (not shown) stores a program for controlling an operation of the processor 30.

The image-capturing device 1000 of FIG. 18 includes an endoscope 600 that is connected to the light source device 100 and the controller 300. The endoscope 600 includes an optical waveguide 60A in which laser light emitted from a speckle variable device 12 of the light source device 100 propagates. The endoscope 600 also includes an optical waveguide 60B in which white light emitted from a white light source 14 propagates. The optical waveguides 60A and 60B are optically connected respectively to illumination optical systems 62A and 62B. A typical example of the optical waveguides 60A and 60B is an optical fiber. The illumination optical systems 62A and 62B emit laser light and white light, respectively, toward an object under study.

The endoscope 600 further includes an imaging device 200, and a signal transmission line 64 that connects the imaging device 200 to the controller 300. An imaging element of the imaging device 200, which is a small-size image sensor, performs imaging on an object of interest, and outputs an image signal. The image signal output from the imaging element is input to the image processing device 32 of the controller 300 through the signal transmission line 64. The image processing device 32 allows the display device 400 to display an image of the object, based on the image signal. In the mode for intentionally observing a speckle pattern, the image processing device 32 can calculate a speckle contrast, and superimpose an image that emphasizes a specific regional segment based on the calculated value.

The processor 30 of the controller 300 sends a control signal for changing a speckle contrast to the speckle variable device 12 according to the operator's input. The speckle variable device 12 changes the coherence of laser light in response to the control signal. When the operator selects a mode that a speckle pattern is most or relatively clearly observed, the actuator 122 of FIG. 8 stops the rotation of the diffuser 120. In a preferable example, laser light is transmitted through the transparent portion 122B of the stopped diffuser 120. As a result, the object is illuminated by highly coherent laser light, and therefore, a speckle pattern having a high contrast can be observed. As described above with reference to FIGS. 6 and 7, the absorption and reflection characteristics of laser light can vary from region to region of an object. Therefore, speckle contrast difference between regions is likely to appear, and therefore, a failure to detect a lesion is prevented or reduced.

Figure 19:
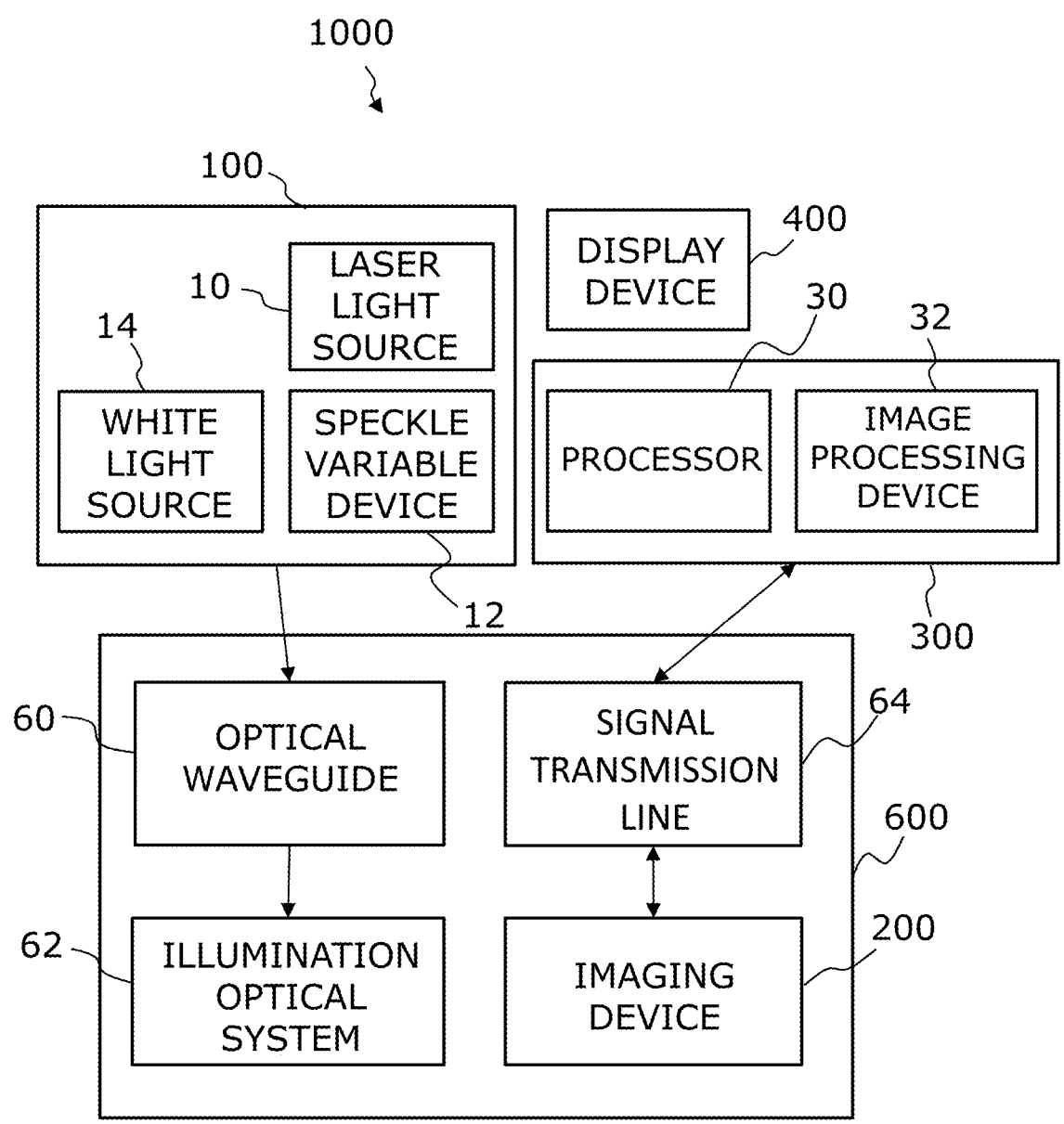
FIG. 19 is a diagram showing another example configuration of an image-capturing device including an endoscope.

FIG. 19 is a diagram showing another example configuration of the image-capturing device 1000. The image-capturing device 1000 of FIG. 14 is different from the image-capturing device 1000 of FIG. 13 in that laser light emitted from the speckle variable device 12 and white light emitted from the white light source 14 both propagate in a common optical waveguide 60, and are emitted from an illumination optical system 62.

Thus, there are various configurations that guide light emitted from the light source device 100 to the distal portion of the endoscope 600, and the present disclosure is not limited to the examples shown. White light can be produced by allowing excitation light that has propagated through the optical waveguide in the endoscope 600 to enter a fluorescent member disposed at the distal portion of the endoscope 600.

The image-capturing device of the present disclosure can be used in various applications for optically obtaining information from an object, and observing the condition of the object. In particular, in the case in which the object is biological tissue, the image-capturing device of the present disclosure can allow obtaining of information from a surface or inner portion of biological tissue in a non-invasive manner, and is therefore useful for an endoscope. The image-capturing device of the present disclosure can also be used in an application such as an industrial endoscope for obtaining useful information from an object other than biological tissue.

The invention claimed is:

1. An image-capturing device comprising:
   an illumination light source configured to emit illumination light to illuminate an object;
   a laser light source configured to emit laser light with a peak wavelength in a range of wavelengths absorbed or reflected by at least one region of the object;
   an imaging device configured to take an image of the object;
   a speckle variable device configured to change a speckle pattern in an image acquired by the imaging device over time by modifying laser light emitted from the laser light source over time; and
   an image processing device configured to process the image acquired by the imaging device, which comprises:
      measuring a change over time in an intensity signal from each pixel constituting the image while the speckle variable device changes the speckle pattern in the image, and
      dividing an imaged region of the object into a plurality of portions based on a waveform of the change in the intensity signal over time.

2. The image-capturing device according to claim 1, wherein the image processing device is configured to calculate a feature of a speckle signal for each of a single pixel or a plurality of pixels based on the waveform of the change in the intensity signal over time, and to allot each of the single or the plurality of pixels to one of the plurality of portions based on the feature.

3. The image-capturing device according to claim 2, wherein the feature is a speckle contrast.

4. The image-capturing device according to claim 2, wherein the image processing device is configured to generate emphasizing image data of an imaged region of the object based on the feature, and to output the emphasizing image data together with image data of the imaged region of the object.

5. The image-capturing device according to claim 1, wherein the peak wavelength of the laser light is in a visible range.

6. The image-capturing device according to claim 5, wherein the imaging device is a color image sensor comprising pixels each comprising an R subpixel, a G subpixel, and a B subpixel, and
wherein the image processing device is configured to select a signal output from at least one subpixel of a color or a plurality of colors comprising a subpixel of a color in a wavelength range covering the peak wavelength of the laser light from among the R subpixel, the G subpixel, and the B subpixel as the intensity signal of each of the pixels.

7. The image-capturing device according to claim 1, wherein the laser light source is a laser diode, and
wherein the speckle variable device comprises a driving circuit configured to modify the laser light emitted from the laser light source over time by driving the laser diode to modulate the laser light over time.

8. The image-capturing device according to claim 1, wherein the object comprises a biological tissue.

9. The image-capturing device according to claim 1, wherein the speckle variable device comprises:
a diffuser disposed in an optical path of the laser light; and
an actuator configured to modify the laser light emitted from the laser light source over time by moving the diffuser to change an incident position of the laser light on the diffuser over time.

10. The image-capturing device according to claim 1, wherein the speckle variable device comprises a moving device configured to modify the laser light emitted from the laser light source over time by changing a relative positional relation of at least one of the laser light source and the imaging device to the object over time.

11. The image-capturing device according to claim 1, comprising:
an endoscope comprising:
a light emitter configured to emit the illumination light and the laser light toward the object; and
a light receiver configured to guide light reflected by the object to the imaging device;
a computation circuit connected to the endoscope and functioning as the image processing device; and
a display device connected to the computation circuit, and configured to display an image of the object divided into the plurality of portions.

* * * * *